(12) United States Patent
Zhang et al.

(10) Patent No.: US 9,957,356 B2
(45) Date of Patent: May 1, 2018

(54) NON-ISOCYANATE POLYURETHANES AND METHODS OF MAKING AND USING THE SAME

(71) Applicant: Elevance Renewable Sciences, Inc., Woodridge, IL (US)

(72) Inventors: Keren Zhang, Blacksburg, VA (US); Ashley M. Nelson, Blacksburg, VA (US); Timothy E. Long, Blacksburg, VA (US); Paul A. Bertin, Woodridge, IL (US); Allyson Beuhler, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days. days.

(21) Appl. No.: 15/234,173

(22) Filed: Aug. 11, 2016

(65) Prior Publication Data

US 2017/0066880 A1  Mar. 9, 2017

Related U.S. Application Data

(60) Provisional application No. 62/206,244, filed on Aug. 17, 2015.

(51) Int. Cl.
*C08G 71/04* (2006.01)
*D06M 15/564* (2006.01)
*C09D 175/04* (2006.01)

(52) U.S. Cl.
CPC ........... *C08G 71/04* (2013.01); *C09D 175/04* (2013.01); *D06M 15/564* (2013.01)

(58) Field of Classification Search
CPC .... C08G 71/04; C09D 175/04; D06M 15/564
See application file for complete search history.

(56) References Cited

U.S. PATENT DOCUMENTS

2015/0247004 A1*  9/2015  Lombardo ............. C08G 71/04
528/371

FOREIGN PATENT DOCUMENTS

| JP | 2014-105219 | 6/2014 |
| WO | 2004/074352 | 9/2004 |
| WO | 2013/010606 | 1/2013 |

OTHER PUBLICATIONS

1. Kathalewar et al "Non-isocyanate polyurethanes: from chemistry to Applications", RSC Adv., 2013, 3, 4110-4129, published on Mar. 2013.*
Tamami et al Incorporation of Carbon Dioxide into Soybean Oil and Subsequent Preparation and Studies of Nonisocyanate Polyurethane Networks, Journal of Applied Polymer Science, vol. 92, 883-891 (2004), published on Jul. 2004.*
Kihara et al "Synthesis and Properties of Poly (hydroxyurethane) s", Journal of Polymer Science: Part A: Polymer Chemistry, vol. 31,2765-2773 (1993), published on Oct. 1993).*
Maisonneuve et al., RSC Adv., vol. 4, pp. 25795-25803 (2014).
Hambali et al., Adv. Mat. Res., vol. 812, pp. 73-79 (2013).
Rokicki et al., Polymers for Adv. Techs., vol. 26(7), pp. 707-761 (2015).
Int'l Search Report & Written Opinion of Int'l Searching Authority, PCT App. No. PCT/US2016/046461, dated Oct. 31, 2016.

* cited by examiner

*Primary Examiner* — Gregory Listvoyb
(74) *Attorney, Agent, or Firm* — Kilpatrick Townsend & Stockton LLP

(57) ABSTRACT

Polyurethane compositions are disclosed herein, as well as methods of making and using such polyesters. In some embodiments, the polyurethanes are formed from monomers derived from natural oils. In some embodiments, the polyurethanes are formed without the use of monomers bearing isocyanate groups.

20 Claims, 4 Drawing Sheets

NON-ISOCYANATE POLYURETHANES AND METHODS OF MAKING AND USING THE SAME

CROSS-REFERENCE TO RELATED APPLICATIONS

The present application claims the benefit of priority of U.S. Provisional Application No. 62/206,244, filed Aug. 17, 2015, which is hereby incorporated by reference as though set forth herein in its entirety.

TECHNICAL FIELD

Polyurethane compositions are disclosed herein, as well as methods of making and using such polyesters. In some embodiments, the polyurethanes are formed from monomers derived from natural oils. In some embodiments, the polyurethanes are formed without the use of monomers bearing isocyanate groups.

BACKGROUND

Polyurethanes are a class of polymers having chains of organic units joined by carbamate linkages, but which can include other linkages as well. Polyurethanes can have a wide variety of physical properties. This is especially the case when polyurethanes are incorporated into block copolymers with other blocks, such as polyethers or polyesters. In some instances, certain blocks are hard or rigid (e.g., the polycarbamate portion) while others are soft and flexible (e.g., the polyester portion). Alteration of the chemical structure, size and/or frequency of these blocks in a polyurethane can allow for modification of the properties of the resin. These options can lead to resins having a wide array of different properties. Some of these resins can be thermosetting, while others can be thermoplastic.

Polyurethane foams can be used for a number of different applications. Polyurethane foams may be flexible or rigid, and can be used in a variety of different applications, including, but not limited to, use for foam insulation, use in packaging materials, and use in cushioning. Polyurethanes can also be used as elastomers. Polyurethane elastomers can be solid or porous, with representative applications including, but not limited to, textile fibers, coatings, sealants, adhesives, and resilient pads. Polyurethanes can also be used as thermosetting polymers. Representative applications of polyurethane thermosets include, but are not limited to, abrasion resistant wheels, mechanical parts, and structural materials.

In many cases, polyurethane synthesis occurs through the reaction of a dibasic acid or ester with a diisocyanate. The use of isocyanates presents certain environmental concerns. Thus, it may be desirable to make polyurethanes without the use of isocyanates.

Meanwhile, refining processes for natural oils (e.g., employing metathesis) can lead to compounds having carbon-chain lengths closer to those generally desired for chemical intermediates of specialty chemicals (e.g., about 9 to 15 carbon atoms). Thus, the refining of natural oils may, in many instances, provide a more chemically efficient and straightforward way to make certain monomers for use in making polymeric species. Further, because such compounds contain a certain degree of inherent functionality that is otherwise absent from petroleum-sourced materials, it may often be more desirable, if not cheaper, to use natural oils or their derivatives as a starting point for making certain compounds. Additionally, natural oils and their derivatives are generally sourced from renewable feedstocks. Thus, by using such starting materials, one can enjoy the concomitant advantage of developing useful chemical products without consuming limited supplies of petroleum.

Thus, there is a continuing need to discover novel monomers for making non-isocyanate polyurethanes, such as monomers derived from renewable sources.

SUMMARY

In a first aspect, the disclosure provides polymers, which comprise constitutional units formed from one of more compounds of Formula (I):

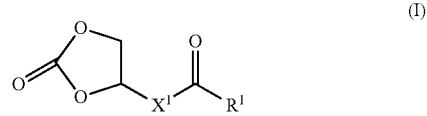

and constitutional units formed from one or more compounds for Formula (II):

wherein $R^1$ is —OH or —OR$^2$, $R^2$ is $C_{1-6}$ alkyl or $C_{1-6}$ oxyalkyl; $X^1$ is $C_{4-10}$ alkylene; and $X^2$ is $C_{4-24}$ alkylene or $C_{4-24}$ heteroalkylene.

In a second aspect, the disclosure provides copolymers that include a first block and a second block, wherein the first block includes a polymer of the first aspect.

In a third aspect, the disclosure provides a coating composition, the composition including polymers of the first aspect or copolymers of the second aspect.

Further aspects and embodiments are provided in the foregoing drawings, detailed description and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

Figure 1:
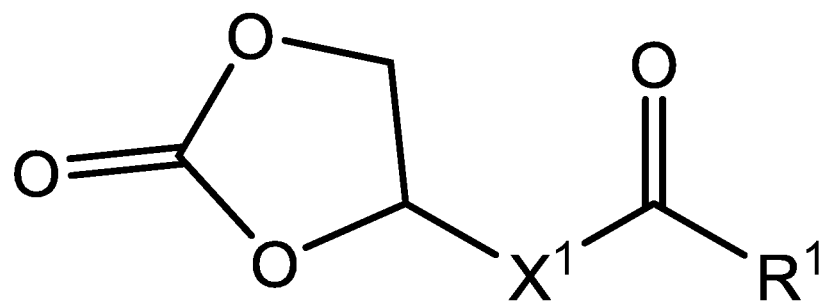
FIG. 1 shows a monomers useful for forming constitutional units making up the polymers disclosed herein, wherein $R^1$ is —OH, alkoxy, or oxyalkyloxy; X' is alkylene; and $X^2$ is alkylene or heteroalkylene.
Figure 1:
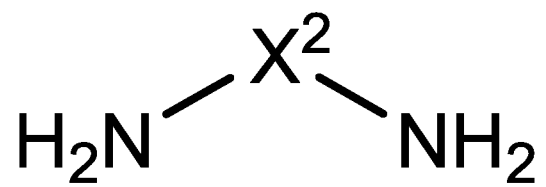

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "polymer" refers to a substance having a chemical structure that includes the multiple repetition of constitutional units formed from substances of comparatively low relative molecular mass relative to the molecular mass of the polymer. The term "polymer" includes soluble and/or fusible molecules having chains of repeat units, and also includes insoluble and infusible networks. As used herein, the term "polymer" can include oligomeric materials, which have only a few (e.g., 5-100) constitutional units As used herein, "monomer" refers to a substance that can undergo a polymerization reaction to contribute constitutional units to the chemical structure of a polymer.

As used herein, "polyester" refers to a polymer comprising two or more ester linkages. Other types of linkages can be included, however. In some embodiments, at least 80%, or at least 90%, or at least 95% of the linkages between monomers in the polyester are ester linkages. The term can refer to an entire polymer molecule, or can also refer to a particular polymer sequence, such as a block within a block copolymer.

As used herein, "copolymer" refers to a polymer having constitutional units formed from more than one species of monomer.

As used herein, "block copolymer" refers to a copolymer having two or more different blocks of polymerized monomers, i.e., different polymer sequences.

As used herein, "polyurethane" or "polycarbamate" refers to a polymer comprising two or more urethane (or carbamate) linkages. Other types of linkages can be included, however. For example, in some instances, the polyurethane or polycarbamate can contain urea linkages, formed, for example, when two isocyanate groups can react. In some other instances, a urea or urethane group can further react to form further groups, including, but not limited to, an allophanate group, a biuret group, or a cyclic isocyanurate group. In some embodiments, at least 70%, or at least 80%, or at least 90%, or at least 95% of the monomer linkages in the polyurethane or polycarbamate are urethane linkages. Further, in the context of a block copolymer, the term "polyurethane block copolymer" refers to a block copolymer, where one or more of the blocks are a polyurethane or a polycarbamate. Other blocks in the "polyurethane block copolymer" may contain few, if any, urethane linkages. For example, in some polyurethane block copolymers, at least one of the blocks is a polyether or a polyester and one or more other blocks are polyurethanes or polycarbamates.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$", which refers to a group of compound having z carbon atoms; and "$C_{x-y}$", which refers to a group or compound containing from x to y, inclusive, carbon atoms. For example, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. As a further example, a "$C_{4-10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the term "low-molecular-weight olefin" may refer to any one or combination of unsaturated straight, branched, or cyclic hydrocarbons in the $C_{2-14}$ range. Low-molecular-weight olefins include alpha-olefins, wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. Olefins in the $C_{4-10}$ range can also be referred to as "short-chain olefins," which can be either branched or unbranched. In one embodiments, it may be preferable to use a mixture of linear and branched $C_4$ olefins (i.e., combinations of: 1-butene, 2-butene, and/or isobutene). In other embodiments, a higher range of $C_{11-14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin ester" or "olefinic ester compounds." Further, a "terminal olefinic ester compound" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "C$_{x-y}$ alkyl," which refers to an alkyl group, as herein defined, containing from x to y, inclusive, carbon atoms. Thus, "C$_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which include groups of the following formulas: -[-(alkylene)-O-]$_x$-alkyl, -[-(alkylene)-O-]$_x$-alkylene-, respectively, where x is 1 or more, such as 1, 2, 3, 4, 5, 6, 7, or 8.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., A1 and A2, then one or more members of the class can be present concurrently.

As used herein, the various functional groups represented will be understood to have a point of attachment at the functional group having the hyphen or dash (–) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Polyurethane Polymers

In a first aspect, the disclosure provides polymers, which comprise constitutional units formed from one of more compounds of Formula (I):

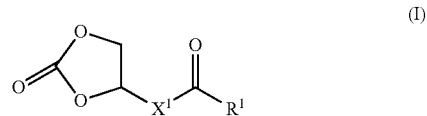

and constitutional units formed from one or more compounds for Formula (II):

wherein R$^1$ is —OH or —OR$^2$; R$^2$ is C$_{1-6}$ alkyl or C$_{1-6}$ oxyalkyl; X$^1$ is C$_{4-10}$ alkylene; and X$^2$ is C$_{4-24}$ alkylene or C$_{4-24}$ heteroalkylene.

In some embodiments of any of the aforementioned embodiments, R$^1$ is —OH. In some other embodiments of any of the aforementioned embodiments, R$^1$ is —OR$^2$. In some such embodiments, R$^2$ is methyl, ethyl, or isopropyl. In some further embodiments, R$^2$ is methyl. In some other such embodiments, R$^2$ is methyl, ethyl, or n-propyl.

In some embodiments of any of the aforementioned embodiments, X$^1$ is —(CH$_2$)$_7$—.

In some embodiments of any of the aforementioned embodiments, X$^2$ is C$_{4-24}$ alkylene. In some such embodiments, X$^2$ is —(CH$_2$)$_4$—, —(CH$_2$)$_6$—, —(CH$_2$)$_8$—, —(CH$_2$)$_{10}$—, —(CH$_2$)$_{12}$—, —(CH$_2$)$_{14}$—, —(CH$_2$)$_{16}$—, —(CH$_2$)$_{18}$—. In some further such embodiments, X$^2$ is —(CH$_2$)$_{12}$—.

In some embodiments of any of the aforementioned embodiments, X$^2$ is C$_{4-24}$ heteroalkylene.

In some embodiments of any of the aforementioned embodiments, X$^2$ is

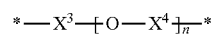

wherein X$^3$ is C$_{1-6}$ alkylene; X$^4$ is C$_{1-6}$ alkylene; and n is an integer from 1 to 500. In some such embodiments, X$^3$ is —(CH$_2$)—, —(CH$_2$)$_2$—, —(CH$_2$)$_3$—, —(CH$_2$)$_4$—, —(CH$_2$)$_5$—, —(CH$_2$)$_6$—, —CH$_2$—CH(CH$_3$)—, or —CH (CH$_3$)—CH$_2$—. In some such embodiments, X$^3$ is —(CH$_2$)$_4$—. In some embodiments, X$^4$ is —(CH$_2$)—, —(CH$_2$)$_2$—, —(CH$_2$)$_3$—, —(CH$_2$)$_4$—, —(CH$_2$)$_5$—, —(CH$_2$)$_6$—, —CH$_2$—CH(CH$_3$)—, or —CH(CH$_3$)—CH$_2$—. In some such embodiments, X$^4$ is —(CH$_2$)$_4$—. In some embodiments, n is an integer from 1 to 200, or from 80 to 120. In some embodiments, n is an integer from 1 to 400, or from 50 to 400, or from 50 to 300, or from 100 to 300.

In some embodiments of any of the aforementioned embodiments, the one or more compounds of Formula (II) include: one or more first diamine compounds wherein X$^2$ is —(CH$_2$)$_4$—, —(CH$_2$)$_6$—, —(CH$_2$)$_6$—, —(CH$_2$)$_{10}$—, —(CH$_2$)$_{12}$—, —(CH$_2$)$_{14}$—, —(CH$_2$)$_{16}$—, or —(CH$_2$)$_{18}$—; and one or more second diamine compounds wherein X$^2$ is

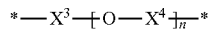

wherein X$^3$, X$^4$, and n have the definitions recited above.

Such polymers can include these two different kinds of diamine compounds in any suitable ratios. For example, in some embodiments, the molar ratio of constitutional units formed from the first diamine compounds to the constitutional units formed from the second diamine compound ranges from 1:100 to 100:1. In some such embodiments, the molar ratio of constitutional units formed from the first diamine compounds to the constitutional units formed from the second diamine compound ranges from 1:10 to 10:1.

The resulting polyurethane polymers can have any suitable molecular weight. For example, in some embodiments, the polyurethane polymers of any of the aforementioned embodiments, have a number-average molecular weight of 2,000 g/mol to 50,000 g/mol.

Polyurethane-Containing Block Copolymers

In certain aspects, the disclosure provides block copolymers, which include a first block and a second block. In some embodiments, the first block includes a polyurethane polymer of any of the aforementioned embodiments. In some embodiments, the second block includes a polyester. In some embodiments, the second block includes a polyether.

Uses

The polyurethane polymers and block copolymers disclosed herein can be used in a wide variety of applications. For example, in certain aspects, the disclosure provides coating compositions that include polyurethane polymers or polyurethane-containing copolymers of any of the aforementioned aspects and embodiments. The polyurethane polymers and copolymers can generally be used in any way that isocyanate-derived polyurethanes are used.

Derivation from Renewable Sources

The compounds employed in any of the aspects or embodiments disclosed herein can, in certain embodiments, be derived from renewable sources, such as from various natural oils or their derivatives. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above).

The conditions for such metathesis reactions, and the reactor design, and suitable catalysts are as described below with reference to the metathesis of the olefin esters. That discussion is incorporated by reference as though fully set forth herein.

The derivation of specific monomer compounds from natural-oil derived materials is illustrated in the Examples below.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above).

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The reactor design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

EXAMPLES

Materials

Methyl 9-decenoate (9-DAME) was provided from Elevance Renewable Sciences, Inc. and used as received. m-Chloroperoxybenzoic acid (m-CPBA, ≤77%), dodecane diamine (98%), lithium bromide (LiBr, ≥99%), 1,5,7-triazabicyclo[4.4.0]dec-5-ene (TBD, 98%), sodium hydroxide solution (NaOH, 1.0 M in water), magnesium sulfate ($MgSO_4$, 99%) sodium sulfite ($NaSO_3$, ≥98%), sodium bicarbonate ($NaHCO_3$, ≥99.7), N-methyl-2-pyrrolidone (NMP, ACS grade), and sodium chloride (NaCl, ≥99%), were obtained from Sigma-Aldrich and used as received. JEFFAMINE THF-100 was poly(tetramethylene oxide)/poly(propylene glycol) copolymer based diamine, obtained from Huntsman Corporation, sample department, and used as received. Bone-dry $CO_2$ was obtained from Airgas and used as received. Ethyl acetate (EtOAc, ACS grade) and dichloromethane (DCM, ACS grade) were purchased from Spectrum Chemicals and used as received. All water used was purified using distillation.

Example 1

Monomer Synthesis

Figure 2:
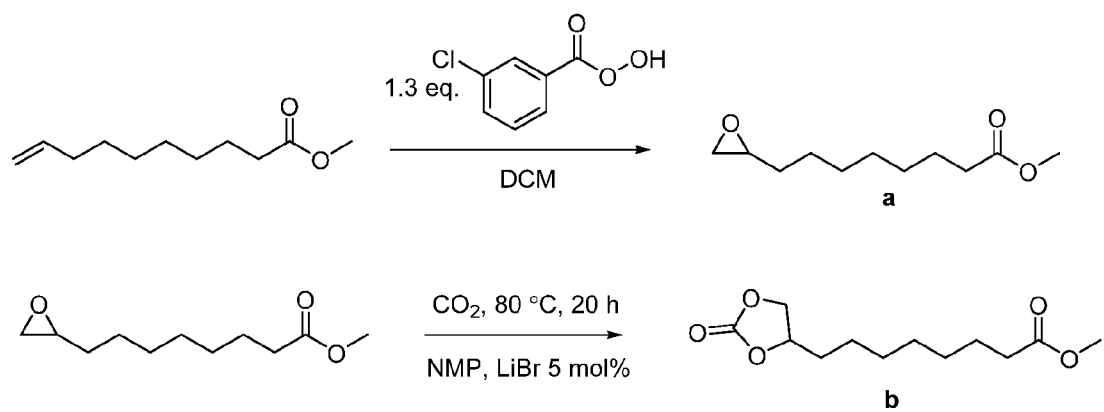
FIG. 2 shows a useful scheme for synthesizing the 9,10-cyclic carbonate-methyl decanoate monomer.

In the first step, m-CPBA (33 g, 0.14 mol) and DCM (200 mL) were added to a 500 mL round-bottomed flask equipped with a magnetic stir bar. The flask was placed into an ice bath with constant stirring until m-CPBA dissolved. 9-DAME (20 g, 0.11 mol) was then added into the solution and allowed to stir overnight. White precipitate was removed from the solution using vacuum filtration. DCM was then removed using a rotary evaporator. Additional white precipitate was removed again with vacuum filtration. The filtrate was washed with saturated $NaSO_3$ solution 2 times, NaOH 1.0 M solution 3 times, $NaHCO_3$ 2 times, and brine 2 times. Light yellow oil was obtained and placed at −20° C. overnight. The oil was filtered through a 5 μm membrane filter and dried in vacuo. The structure and purity of obtained methyl 9,10-epoxydecanoate intermediate a (FIG. 2) were confirmed using NMR spectroscopy and mass spectroscopy. In the second step, methyl 9,10-epoxydecanoate (4.0 g, 20 mmol), NMP (10 mL), and LiBr (0.087 g, 1.0 mmol) were added into a 100 mL round-bottomed flask equipped with a magnetic stir bar. The reaction mixture was stirred at 80° C. with constant CO$_2$ bubbling for 24 h. After cooling back to room temperature, the reaction mixture was dissolved in 100 mL EtOAc and washed with 150 mL brine. The organic phase was dried with MgSO$_4$ and rotatory evaporated to remove EtOAc. Resulted light brown oil was dried in vacuo at 50° C. for 24 h and cooled to room temperature to obtain a salmon color solid (4.9 g, 89% yield). This reaction is illustrated in FIG. 2.

Example 2

Polymerization

Figure 3:
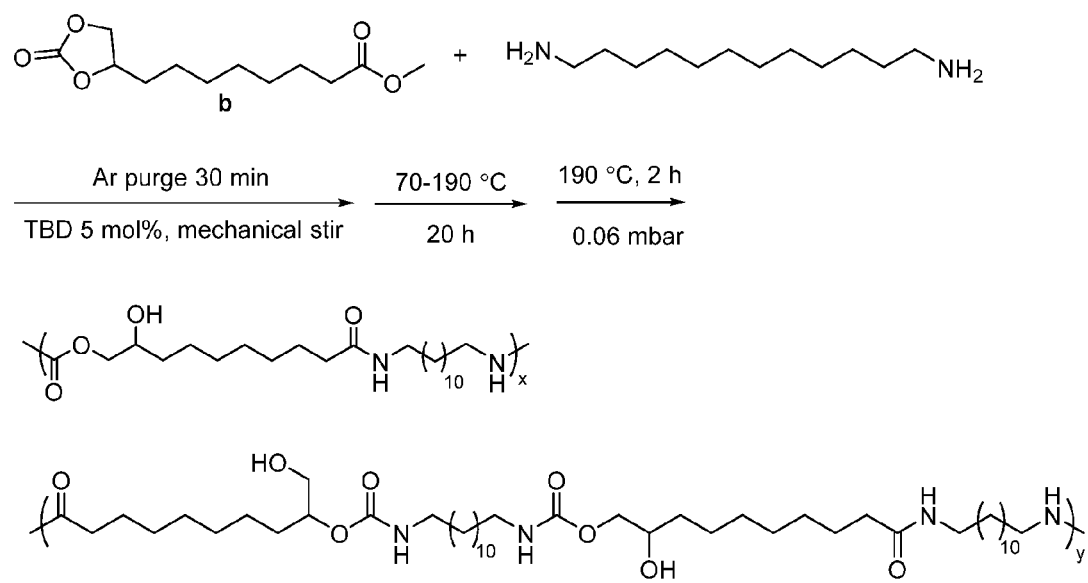
FIG. 3 shows a useful scheme for the one-pot melt polymerization of non-segmented poly(amide-hydroxyurethane) (PAHU).

First, 9,10-cyclic carbonate-methyl decanoate b (2.0 g, 8.2 mmol), dodecane diamine (2.5 g, 8.9 mmol), and TBD (0.057 g, 0.41 mmol) were charged to a dry, 100 mL round-bottomed flask. The flask was equipped with an overhead stir rod, argon inlet, and connection to vacuum. After argon purge for 30 min, the flask was heated to 70° C. to allow melting of the solids. The flask was then heated from 70° C. to 190° C. with constant stirring over 24 h, and the pressure was subsequently reduced to 0.06 mbar at 190° C. for additional 2 h. The resulting polymer was collected without further purification. This reaction is illustrated in FIG. 3.

Example 3

Polymerization

Figure 4:
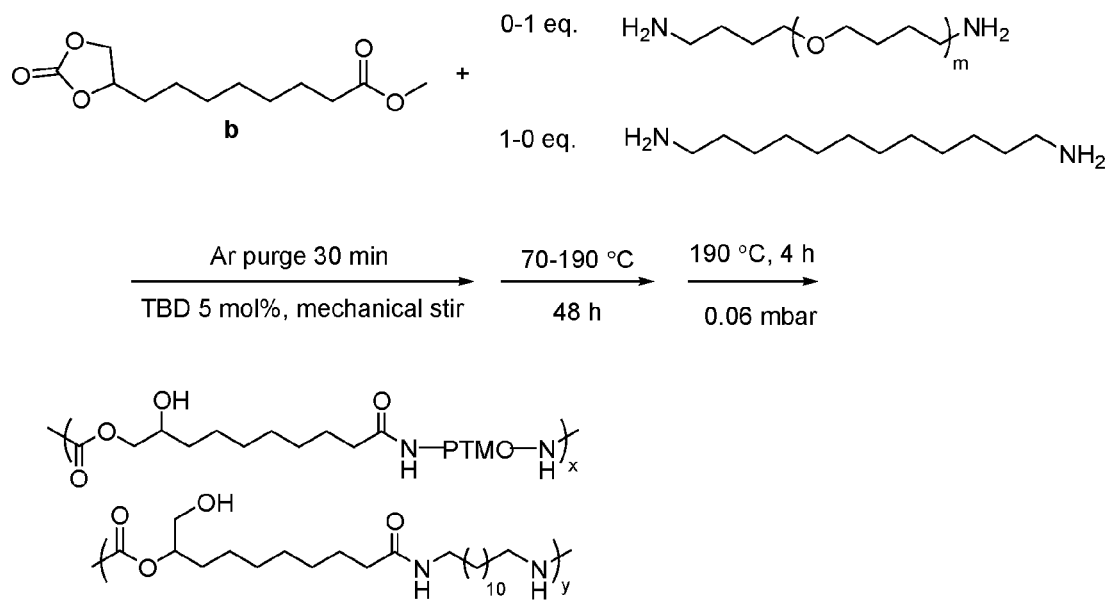
FIG. 4 sows a useful scheme for the one-pot melt polymerization of segmented PAHU-PTMO.

A polymerization of segmented PAHU-PTMO was conducted as following: 9,10-cyclic carbonate-methyl decanoate b (2.0 g, 8.2 mmol), dodecane diamine (0.84 g, 4.2 mmol), PTMO-diamine (THF-100 JEFFAMINE) (4.2 g, 4.1 mmol) and TBD (0.057 g, 0.41 mmol) were charged to a dry, 100 mL round-bottomed flask. The flask was equipped with an overhead stir rod, argon inlet, and connection to vacuum. After argon purge for 30 min, the flask was heated to 70° C. to allow melting of the solids. The flask was then heated from 70° C. to 180° C. with constant stirring over 24 h, and the pressure was subsequently reduced to 0.06 mbar at 180° C. for additional 4 h. The resulting polymer was collected without further purification. This reaction is illustrated in FIG. 4.

What is claimed is:

1. A polymer, which comprises constitutional units formed from one of more compounds of Formula (I):

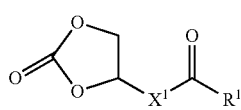
(I)

and constitutional units formed from one or more compounds for Formula (II):

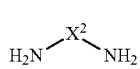
(II)

wherein:
R$^1$ is —OH or —OR$^2$;
R$^2$ is C$_{1-6}$ alkyl or C$_{1-6}$ oxyalkyl;
X$^1$ is C$_{4-10}$ alkylene; and
X$^2$ is C$_{4-24}$ alkylene or C$_{4-24}$ heteroalkylene.

2. The polymer of claim 1, wherein R$^1$ is —OH.
3. The polymer of claim 1, wherein R$^1$ is —OR$^2$.
4. The polymer of claim 3, wherein R$^2$ is methyl, ethyl, or isopropyl.
5. The polymer of claim 3, wherein R$^2$ is methyl.
6. The polymer of claim 1, wherein R$^2$ is methyl, ethyl, or n-propyl.
7. The polymer of claim 1, wherein X$^1$ is —(CH$_2$)$_7$—.
8. The polymer of claim 1, wherein X$^2$ is C$_{4-24}$ alkylene.
9. The polymer of claim 8, wherein X$^2$ is —(CH$_2$)$_4$—, —(CH$_2$)$_6$—, —(CH$_2$)$_8$—, —(CH$_2$)$_{10}$—, —(CH$_2$)$_{12}$—, —(CH$_2$)$_{14}$—, —(CH$_2$)$_{16}$—, —(CH$_2$)$_{18}$—.
10. The polymer of claim 9, wherein X$^2$ is —(CH$_2$)$_{12}$—.
11. The polymer of claim 1, wherein X$^2$ is C$_{4-24}$ heteroalkylene.
12. The polymer of claim 11, wherein X$^2$ is

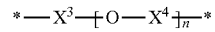

wherein
X$^3$ is C$_{1-6}$ alkylene;
X$^4$ is C$_{1-6}$ alkylene;
n is an integer from 1 to 500.
13. The polymer of claim 12, wherein X$^3$ is —(CH$_2$)—, —(CH$_2$)$_2$—, —(CH$_2$)$_3$—, —(CH$_2$)$_4$—, —(CH$_2$)$_5$—, —(CH$_2$)$_6$—, —CH$_2$—CH(CH$_3$)—, or —CH(CH$_3$)—CH$_2$—.
14. The polymer of claim 13, wherein X$^3$ is —(CH$_2$)$_4$—.
15. The polymer of claim 12, wherein X$^4$ is —(CH$_2$)—, —(CH$_2$)$_2$—, —(CH$_2$)3 —, —(CH$_2$)$_4$—, —(CH$_2$)$_5$—, —(CH$_2$)$_6$—, —CH$_2$—CH(CH$_3$)—, or —CH(CH$_3$)—CH$_2$—.
16. The polymer of claim 15, wherein X$^4$ is —(CH$_2$)$_4$—.
17. The polymer of claim 12, wherein n is an integer from 80 to 120.
18. The polymer of claim 1, wherein the one or more compounds of Formula (II) comprises:
one or more first diamine compounds wherein X$^2$ is —(CH$_2$)$_4$—, —(CH$_2$)$_6$—, —(CH$_2$)$_8$—, —(CH$_2$)$_{10}$—, —(CH$_2$)$_{12}$—, —(CH$_2$)$_{14}$, —(CH$_2$)$_{16}$—, —(CH$_2$)$_{18}$—; and
one or more second diamine compounds wherein X$^2$ is

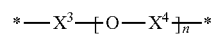

wherein X$^3$, X$^4$, and n have the definitions recited above.
19. The polymer of claim 18, wherein the molar ratio of constitutional units formed from the first diamine compounds to the constitutional units formed from the second diamine compound ranges from 1:100 to 100:1.
20. The polymer of claim 19, wherein the molar ratio of constitutional units formed from the first diamine compounds to the constitutional units formed from the second diamine compound ranges from 1:10 to 10:1.

* * * * *